United States Patent [19]

Singh

[11] 3,944,608

[45] Mar. 16, 1976

[54] SYNTHESIS OF N-[1-(CHLOROMETHYL)PROPYL]ACETAMIDE

[75] Inventor: Balwant Singh, Stamford, Conn.

[73] Assignee: American Cyanamid Company, Stamford, Conn.

[22] Filed: Aug. 1, 1974

[21] Appl. No.: 493,800

[52] U.S. Cl.......................... 260/561 HL; 260/561 R
[51] Int. Cl.[2]........................................ C07C 103/34
[58] Field of Search................... 260/561 R, 561 HL

[56] References Cited
UNITED STATES PATENTS

| | | | |
|---|---|---|---|
| 2,569,549 | 10/1951 | Barrick | 260/584 R |
| 3,855,300 | 12/1974 | Takahashi et al. | 260/561 R |

*Primary Examiner*—C. Davis
*Attorney, Agent, or Firm*—Samuel Branch Walker

[57] ABSTRACT

N-[1-(Chloromethyl)propyl]acetamide, for the synthesis of ethambutol hydrochloride, d,d'-2,2'-(ethylenediimino)-di-1-butanol dihydrochloride, is produced in high purity and good yields by the reaction of butene-1, a nitrile, preferably an excess of acetonitrile, and chlorine to form N-[1-(chloromethyl)propyl]acetimidoyl chloride which is hydrolyzed to N-[1-(chloromethyl)propyl]acetamide. This may be hydrolyzed further to dl-2-amino-1-butanol, which can be isolated as the hydrochloride, or free base, or a mixture, resolved with L(+)-tartaric acid and the d-2-amino-1-butanol reacted with ethylene dichloride and then hydrochloric acid to form ethambutol hydrochloride.

6 Claims, No Drawings

SYNTHESIS OF
N-[1-(CHLOROMETHYL)PROPYL]ACETAMIDE

BACKGROUND OF THE INVENTION

Ethambutol hydrochloride, which is d,d'-2,2-(ethylenediimino)di-1-butanol dihydrochloride is a therapeutic agent for the treatment of tubercle bacilli infections, particularly human tuberculosis caused by *Mycobacterium tuberculosis*. The compound, its preparation, and its therapeutic use are disclosed in U.S. Pat. No. 3,176,040, 1965, Wilkinson and Shepherd, see Example 2 thereof. The therapeutic activity of the d-isomer is discussed in J. Am. Chem. Soc. 83, 2212 (1961).

The d,d-form of ethambutol may be made by reacting ethylene dichloride with d-2-amino-1-butanol. The ethambutol can be separated as the base, and converted to the dihydrochloride salt.

One method of resolving aminobutanol is disclosed in U.S. Pat. No. 3,553,257, Jan. 5, 1971, Halmos and Ricketts.

U.S. Pat. No. 3,769,347, Oct. 30, 1973, John Kazan, PRODUCTION OF d,d'-2,2'-(ETHYLENEDIIMINO)DI-1-BUTANOL HYDROCHLORIDE, details certain processes for the improvement of yields and purity. Said patents and publications are herein hereby incorporated by this reference thereto.

PRIOR ART

U.S. Pat. No. 2,569,549, Oct. 2, 1951, P. L. Barrick, IMIDOHALIDES AND PROCESS OF PREPARING THEM AND THEIR HYDROLYSIS PRODUCTS, discloses the preparation of imidohalides of N-acyl-beta-haloamines. Among much other disclosure, Example VIII discloses the reaction of 56 parts (0.5 mole) of octene-1, 41 parts (1 mole) of acetonitrile and 55 parts (0.77 mole) of chlorine at 10°–15° C., with the reaction mixture being poured into ice and water, treated with concentrated hydrochloric acid, and steam distilled.

The product reported is 14 parts of the hydrochloride of 1-hydroxymethylheptylamine

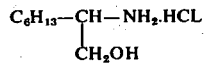

produced by the complete hydrolysis of the intermediate imidochloride of N-[(alpha-hexyl-beta-chloro)ethyl]acetamide. Using the nomenclature of this case, these would be named dl-2-amino-1-octanol hydrochloride and N-[1-(chloromethyl)heptyl]-acetimidoyl chloride. Column 12, line 75, mentions butene-1, among other starting materials.

Example VI of said U.S. Pat. No. 2,569,549 shows the addition of isobutylene to a solution of 32 parts of chlorine in 135 parts of acetonitrile, until the yellow color disappeared. Excess acetonitrile was removed, and the product was hydrolyzed with dilute hydrochloric acid to produce an N-(chloroisobutyl)-trichloroacetamide, probably N-[(beta-chloro-alpha, alpha-dimethyl)ethyl]trichloroacetamide.

SUMMARY OF THE INVENTION

N-[1-(Chloromethyl)propyl]acetamide is prepared by adding butene-1 and chlorine to acetonitrile, preferably simultaneously, to yield N-[1-(chloromethyl)propyl]acetimidoyl chloride together with a certain amount of by-product 1,2-dichlorobutane, the N-[1-(chloromethyl)propyl]acetimidoyl chloride is hydrolyzed to give N-[1-(chloromethyl)propyl]acetamide. One utility for N-[1-(chloromethyl)propyl]acetamide is further hydrolysis with presumably a ring closing and reopening steps to dl-2-amino-1-butanol, conveniently as the hydrochloride. The dl-2-amino-1-butanol hydrochloride may be resolved into its optical isomers with the d-2-amino-1-butanol being reacted with ethylene dichloride to produce ethambutol hydrochloride, d,d'-2,2'-(ethylenediimino)di-1-butanol dihydrochloride. Good yields of a pharmaceutically elegant elegant product are readily obtained.

This gives d-2-amino-1-butanol in a form which is particularly acceptable for reaction with ethylene dichloride to yield a pharmaceutically elegant grade of d,d'-2,2'-(ethylenediimino)di-1-butanol dihydrochloride.

These equations may be written:

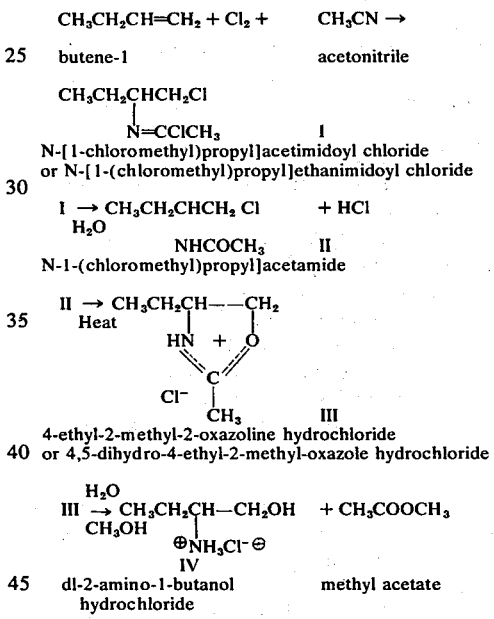

Surprisingly, best results are obtained in the reaction with acetonitrile if an excess of acetonitrile is used. Acetonitrile is the expensive component and routinely it is customary to attempt to use less of the expensive component.

Here, chlorine also reacts with butene-1 to yield 1,2-dichlorobutene. An excess of acetonitrile shifts the reaction towards N-[1-(chloromethyl)propyl]acetimidoyl chloride. An amount of water corresponding to that required for the hydrolysis of N-[1-(chloromethyl)propyl]acetimidoyl chloride may be added before, with or after the addition of the chlorine and butene to the reaction mixture to hydrolyze the N-[1-chloromethyl)propyl]acetimidoyl chloride to N-[1-(chloromethyl)-propyl]acetamide. The reaction of acetonitrile with hydrochloric acid formed in the hydrolysis is sufficiently slow that at least 95 percent of the excess of acetonitrile may be distilled under reduced pressure from the reaction mixture and recycled. The economical recovery of the acetonitrile in such form that it may be recycled to the process is essential to the low cost production being sought.

Too great an excess of acetonitrile requires too large a reaction vessel. A continuous reaction may be used, which permits smaller equipment, and a large excess of acetonitrile, which is recycled to the starting materials.

After stripping the acetonitrile, if hydrolysis of N-[1-(chloromethyl)propyl]acetimidoyl chloride to N-[1-(chloromethyl)propyl]acetamide has not been completed during the reaction, hydrolysis is completed by adding water to the pot residue. Production of N-[1-(chloromethyl)propyl]acetamide by hydrolysis of N-[1-(chloromethyl)propyl]acetimidoyl chloride, is favored by the presence of a weak base such as calcium carbonate, calcium oxide, calcium hydroxide, sodium carbonate, sodium bicarbonate, potassium carbonate or bicarbonate, barium carbonate, or strontium carbonate. The base is not necessary if the N-[1-(chloromethyl)propyl]acetamide is to be processed by further hydrolysis to dl-2-amino-1butanol. After hydrolysis, 1-2-dichlorobutane is stripped by distillation under reduced pressure.

After removal of the acetonitrile and 1,2-dichlorobutane, the purity of the N-[1-(chloromethyl)propyl]acetamide is sufficiently high for convenient processing through to dl-2-amino-1-butanol hydrochloride of a grade which may be used in a resolution step, or other purposes.

The N-[1-(chloromethyl)propyl]acetimidoyl chloride may be recovered and utilized after its formation. Conveniently, water is added to the reactor to hydrolyze N-[1-(chloromethyl)propyl]acetimidoyl chloride to N-[1-(chloromethyl)-propyl]acetamide, so that, in effect, the first two steps are simultaneously accomplished, exotherms are better controlled, and the processing steps are simultaneous, saving time and manipulation. A slight excess over the calculated quantity of water necessary for hydrolysis of N-[1-(chloromethyl)-propyl]acetimidoyl chloride to N-[1-(chloromethyl)-propyl]-acetamide may be added after the completion of chlorination.

The acetonitrile may be separated from the N-[1-(chloromethyl)propyl]acetimidoyl chloride or N-[1-(chloromethyl)propyl]acetamide. Conveniently, it is separated after the hydrolysis to N-[1-(chloromethyl)-propyl]acetamide. The 1,2-dichlorobutane may be separated in whole or in part by distillation after the synthesis of N-[1-(chloromethyl)propyl]-acetimidoyl chloride, or after hydrolysis to N-[1-(chloromethyl)-propyl]acetamide. At least part of the 1,2-dichlorobutane may be retained until the synthesis of the dl-2-amino-1-butanol hydrochloride is completed. It is usually more convenient to separate the 1,2-dichlorobutane after the hydrolysis to the N-[1-chloromethyl)-propyl]acetamide, as the reaction mixture is then smaller, and more compact equipment may be used for the reaction of the N-[1-(chloromethyl)-propyl]acetamide to dl-2-amino-1-butanol hydrochloride. Azeotropic distillation with water permits convenient and effective complete removal of the 1,2-dichlorobutane from the dl-2-amino-1-butanol.

Subsequently, methanol is added to the aqueous reaction mixture containing N-[1-(chloromethyl)propyl]acetamide, preferably with catalytic amounts of hydrochloric acid, which is refluxed to hydrolyze to dl-2-amino-1-butanol hydrochloride with by-product methyl acetate. The methyl acetate is removed by distillation leaving dl-2-amino-1-butanol hydrochloride.

For the production of N-[1-(chloromethyl)propyl]-acetimidoyl chloride, the presence of water is to be avoided, and vacuum distillation to remove acetonitrile and 1,2-dichlorobutane is necessary. If hydrolyzed to N-[1-chloromethyl)propyl]acetamide, mild conditions for the removal of both acetonitrile and 1,2-dichlorobutane are preferred. A weak base aids in controlled hydrolysis. Where hydrolysis to dl-2-amino-1-butanol is desired, the acid produced in hydrolysis can be used to form the hydrochloride salts of the product.

In the production of dl-2-amino-1-butanol hydrochoride, the acetonitrile should be vacuum distilled out at the N-[1-(chloromethyl)propyl]acetamide stage, for recycling. If the acetonitrile is permitted to remain during the hydrolysis to dl-2-amino-1-butanol hydrochloride, the acetonitrile tends to hydrolyze to acetic acid with production of ammonia, usually as the ammonium chloride. The acetic acid from the hydrolysis of acetonitrile is readily removed as the methyl ester, but the loss of acetonitrile reduces the efficiency of the process.

1,2-dichlorobutane is preferably at least partially removed by vacuum distillation at the N-[1-(chloromethyl)-propyl]acetamide stage. It causes no complications other than increasing the size of the reactor required. Conveniently, the last of the 1,2-dichlorobutane is removed by azeotropic distillation from dl-2-amino-1-butanol hydrochloride at the time acetic acid is removed as the methyl ester. Conveniently, the intermediate reactions to dl-2-amino-1-butanol hydrochloride may overlap without the isolation of N-[1-(chloromethyl)propyl]acetimidoyl chloride and N-[1-(chloromethyl)propyl]acetamide.

By dissolving in methyl alcohol, or isopropanol, or mixtures thereof, a solution of the dl-2-amino-1-butanol, predominantly as the hydrochloride, is obtained which can be partially neutralized with ammonia to form a mixture of dl-2-amino-1-butanol and dl-2-amino-1-butanol hydrochloride, with ammonium chloride being filtered out. The mixture is approximately two parts dl-2-amino-1-butanol and one part dl-2-amino-1-butanol hydrochloride, a ratio which is close to the optimum desired for reacting with L(+)- tartaric acid in the presence of anhydrous methanol to permit the separation of the d-2-amino-1-butanol tartrate as is set forth in detail in U.S. Pat. No. 3,553,257, supra.

This process has unique and unexpected advantages in the present system because part of the butene-1adds chlorine and acetonitrile in the reverse of the desired position so that about 3 to 10% dl-1-amino-2-butanol is found in the dl-2-amino-1-butanol as an impurity. In separation of the d- and l -isomers of dl-2-amino-1-butanol, both isomers of dl-1-amino-2-butanol remain with the mother liquor, and a much purified d-2-amino-1-butanol separates out as the L(+)- tartrate salt.

A starting material containing up to about 10% of dl-1-amino-2-butanol yields a purified d-2-amino-1-butanol, as the tartrate, having a content of less than 0.01% of dl-1-amino-2-butanol, as its tartrate salts. If washing is less thorough, up to 0.1 percent may be present. A purity is readily obtained which can be used as a starting material for ethambutol which is of pharmaceutical grade with a minimum of additional purification.

The facility of separating out impurities and by-products is unobvious and of the essence of the present system of reactions.

EXAMPLE 1

Preparation of dl-2-Amino-1-butanol hydrochloride

Acetonitrile (164 g., 4 moles) is placed in a tared 500 ml 4-necked Morton flask equipped with a mechanical stirrer, a thermometer, two fritted glass gas-inlet tubes, a syringe needle (attached to a syringe pump), and a dry-ice condenser. The flask is cooled in an ice-water bath to 3°–5°C. Chlorine (71 g., 1 mole) and butene-1 (56 g. 1 mole) are passed through the well-stirred acetonitrile at a rate of about 400 ml./min. each while water (10 g., 0.55 mole) is added simultaneously at a linear rate with the syringe pump during the course of the reaction (1 hour).

The reaction temperature rises to 20°C. within 8 minutes and stays constant through the course of the reaction. The reaction mixture is stirred for an additional 15–30 minutes. The reaction mixture is weighed to insure that proper amounts of the gaseous reactants have been introduced. Excess acetonitrile (b.p. 36°–41°C./150–170 mm.) is removed by distillation (bath temperature up to 100°C.) while using a 10-plate distillation column. A sudden temperature drop indicates the end of acetonitrile distillation.

The acetonitrile fraction contains 1–2% HCl and about 6% 1,2-dichlorobutane and can be recycled, without further treatment to a subsequent batch, or can be purified before recycling.

The head temperature rises to 70° and by-product 1,2-dichlorobutane is distilled off between 70°–40° C. at 150 to 25 mm. A dry-ice trap attached to the vacuum line contains 15–25 g. of a material which consisted of 35% HCl, 10% 1,2-dichlorobutane and a crystalline solid derived from the reaction of acetonitrile with anhydrous HCl.

The residue in the flask, predominantly N-[1-(chloromethyl)propyl]acetamide, is mixed with water (45 g. 2.5 moles) and the mixture is brought to reflux. The residual 1,2-dichlorobutane is removed by azeotropic distillation (Dean-Stark trap) while the mixture is refluxed for 2 hours. The water and some acetic acid (formed during hydrolysis with water) are removed at 80° (under reduced pressure (15–20 mm.) to leave a viscous residue consisting of N-[1-(chloromethyl)-propyl]acetamide, and its hydrolysis products.

Methanol (48 g., 1.5 moles) and concentrated hydrochloric acid (0.5 ml) are added to the residue and the reaction mixture is refluxed for 2 hours. After removal of the volatiles (H$_2$O, methyl acetate, etc.), the dl-2-amino-1-butanol hydrochloride is obtained as a colorless viscous material which crystallizes on standing.

EXAMPLE 2 dl-2-amino-1-butanol

A 30 g. portion of the crude dl-2-amino-1-butanol hydrochloride from Example 1 is suspended in a mixture of 100 ml. of toluene and 20 ml. of isopropanol. Anhydrous ammonia (10.2 g., 0.6 mole) is introduced over the surface of the well-stirred suspension at 25° C. A dry ice-acetone condenser controls ammonia loss during reaction. Crystalline ammonium chloride starts precipitating immediately and stirring is continued for 15–20 minutes to insure completion of the reaction. The dry ice-acetone condenser is removed and excess NH$_3$ is allowed to volatilize (15–20 minutes). The precipitated NH$_4$Cl is filtered off and washed with a small amount of toluene.

The filtrate and washings are combined and the solvents evaporated under reduced pressure to obtain d,1-2-amino-1-butanol (21.0 g.). The product by gas liquid chromatography is 63 percent pure, and contains about 8% of dl-1-amino-2-butanol. The same process can be used to obtain the d- or l- optical isomer as a free base from its hydrochloride salt.

EXAMPLE 3 d-2-amino-1-butanol tartrate from dl-2-amino-1-butanol hydrochloride

A 50 g. sample of dl-2-amino-1-butanol hydrochloride from Example 1 is dissolved in 100 ml. of anhydrous methanol. One mole of anhydrous NH$_3$ is condensed in over a period of 40 minutes. (A dry ice-acetone condenser is used to prevent ammonia loss during reaction). After stirring for 0.5 hr., the dry ice-acetone condenser is removed and excess NH$_3$ is allowed to volatilize (20–30 minutes). The precipated NH$_4$Cl is filtered off (13.2 gm., 0.246 mole, 62%) and the filtrate is concentrated to leave a viscous oil (43 gm.) which contains 58% by weight free dl-2-amino-1-butanol (the remainder being unreacted dl-2-amino-1-butanol hydrochloride).

The mixture (42 g.) is dissolved in 120 ml. of anhydrous methanol and the solution is treated with 35 g. (0.233 mole) of L(+)- tartaric acid. The reaction temperature rises to 45°–47° C. during addition of tartaric acid. The solution is maintained at this temperature for 1 hour and then cooled to 25°C. over a period of 4–5 hours. Crystallization can be expedited by seeding the solution with d-2-amino-1-butanol L(+)- tartrate to induce crystallization of the salt.

The precipitated salt is filtered off and washed four times with cold methanol and then dried in an inert atmosphere. The salt is obtained as colorless crystalline solid (30 g., 0.125 mole, 63 percent) mp. 138°–140°C-.$[\alpha]_D^{26} = 23.52°$ ($c=5\%$,H$_2$O) and in a typical run was indistinguishable from authentic d-2-amino-1-butanol L(+)- tartrate [mp. 137°–141°C.; $[\alpha]_D^{26} = 23.74°$($c=5\%$,H$_2$O)]. Up to about 8% of dl-1-amino-2-butanol may be formed in the reactions from the addition of the imido group to the 1 position in butene-1, in effect, the reverse of that desired. By analogous reactions, this is converted to dl-1-amino-2-butanol. Both the d and l isomers remain with the mother liquor in the crystallization, and permit the separation of d-2-amino-1-butanol L(+)- tartrate substantially free from impurities.

The isolation of d-2-amino-1-butanol from the salt has been described in U.S. Pat. No. 3,553,257, supra.

Conversion to ethambutol is described in U.S. Pat. No. 3,769,347, supra.

EXAMPLE 4 d-2-Amino-1-butanol d-2-Amino-1-butanol tartrate (150 g.) (0.63 mole) from Example 3 is added with stirring to an aqueous solution of KOH prepared by dissolving 76 g. KOH in 115 ml. of distilled water. d-2-Amino-1-butanol which forms the upper layer is extracted with tetrahydrofuran (100 ml. × 2). The tetrahydrofuran extract is dried (Na$_2$SO4) and concentrated under reduced pressure. The crude, oily residue is distilled under reduced pressure to give d-2-amino-1-butanol (b.p. 99°–103° at 30 mm.). The material is further fractionated to give pure d-2-amino-1-butanol having a b.p. of 174°, and $[\alpha]_D^{25} =$ 9.9. The yield of the distilled material is about 50 percent to 76 percent and can be improved substantially if additional extractions are carried out with tetrahydrofuran.

EXAMPLE 5

Ethambutol Hydrochloride

Following the procedure described in Example 1 of U.S. Pat. No. 3,769,347, a mixture of 462 g. of d-2-amino-1-butanol, produced in accordance with the procedure of Example 4, and 32 g. of ethylene dichloride is heated to 80°C. and the temperature is allowed to rise exothermally to about 130°C. After 1 hour, the mixture is cooled to about 95°C., 22.5 g. of sodium hydroxide is slowly added, and a temperature of about 112°C. is maintained for 1 hour. The sodium hydroxide is in the form of prills of about 4 mm. diameter. The mixture is cooled to 70°C. and unreacted d-2-amino-1-butanol is recovered by vacuum distillation. The distillation is at a pressure below 20 mm. mercury, and below 130°C., heat being applied at a rate within the capacity of the condenser.

Isopropanol (290 g.) is added to the distillation residue at a temperature not above 90°C., and followed by a refluxing period of 30 minutes. The mixture is cooled to and filtered at 60°C. to remove sodium chloride, and the filter cake is washed with 47 g. of isopropanol, at 60°C. The volume of the filtrate is diluted to 430 ml. with isopropanol and the temperature is adjusted to 40°–45°C., 2 g. of diatomaceous earth filter aid is added, and a second filtration is carried out.

To the clear filtrate there is added 120 g. of methanol and 15 g. of water. The vessel is closed and hydrogen chloride (about 25 g.) is introduced over the surface of the charge at a gas pressure of 5–7 p.s.i.g. while the temperature is allowed to rise to 55°C., to a pH of 2 to 2.5. The charge is cooled very slowly to 28°C. and is stirred for about 1 hour.

Conveniently, a small aliquot is titrated, and a calculated quantity of hydrogen chloride added. Proper final pH is confirmed by testing as acid to wet Congo Red test paper. Other methods of measuring the pH can be used. The while crystalline product, d,d'-2,2'-(ethylenediimino)-di-1-butanol dihydrochloride is separated by filtration and washed with isopropanol. The product, carefully dried at a maximum temperature of 75°C., is about 70 g., has a decomposition range of 198.5°–204°C., and an ash content of 0.1 percent.

This is a pharmaceutically acceptable, elegant grade of ethambutol hydrochloride without further treatment or refinement. The product may be tabletted or encapsulated by conventional procedures.

EXAMPLE 6

N-[1-(Chlormethyl)propyl]acetamide

Into a 250 ml. 3-necked flask fitted with a stirrer, dry ice-acetone trap, a gas outlet, and a gas inlet is charged 41.05 g. (1.0 mole) acetonitrile, 25 g. (0.25 mole) $CaCO_3$, 13.5 ml. (0.75 mole) water and 26.8 g. (0.475 mole) 1-butene. The mixture is cooled to $-5°$ to $-8°C$. and chlorine added over 2 hours maintaining the temperature at below 7°C. until the reaction mixture turns yellow indicating a slight excess of chlorine. The mixture is filtered and the solvents distilled under reduced pressure to yield 28.6 g. of N-[1-(chloromethyl)propyl]acetamide (40.2 percent yield based on 1-butene).

EXAMPLE 7

N-[1-(Chloromethyl)propyl]acetamide

A 500 ml. 3-necked flask fitted with a stirrer and dry ice-acetone trap is charged with 82.1 g. (2.0 mole) acetonitrile, 27.4 g. (1.52 mole) water, 27 g. (0.25 mole) $Na_2CO_3$ and 28.1 g. (0.50 mole) 1-butene and cooled to 0°C. Chlorine (0.50 mole) is added over ½ hour, the reaction temperature reaching a high of 32°C. After stirring for 2 hours at 25°C., the reaction mixture is filtered. The acetonitrile washings of the solid phase and filtrate is combined and the solvents removed by vacuum distillation to leave 33.0 g. of the N-[1-(chloromethyl)propyl]acetamide (44.0 percent yield based on 1-butene).

EXAMPLE 8 dl-2-Amino-1-butanol

Sodium hydroxide pels (97% pure, 18.8 g. 0.45 mole) are stirred with 100 ml. of anhydrous methanol and crude dl-2-amino-1-butanol hydrochloride 50 g. (87% real. 0.35 mole) from a run similar to that of Example I is added with stirring over a period of 0.5 hr. The reaction mixture warms up and precipitated sodium chloride is removed by filtration, washed with methanol and the washings combined with the main filtrate. Methanol and water (formed during neutralization) are removed under reduced pressure and the residual oil distilled to yield dl-2-amino-1-butanol (b.p. 95°–100°/30-35 mm.), 26.68 g. (86 percent of theory). The material contains about 9.6% of dl-1-amino-2-butanol.

dl-2-Amino-1-butanol can be used as a catalyst as described in U.S. Pat. No. 3,539,652 (CA 74, 23499) as a component of organosilicone compositions, French Pat. No. 1,556,008 (CH71, 115) or as a component in a flame retardant composition U.S. Pat. No. 3,413,380 (CA 70, 40).

EXAMPLE 9 dl-2-Amino-1-butanol

Sodium hydroxide pels (97 percent pure, 18.8 g. 0.45 mole) are stirred with 100 ml. of isopropanol containing 0.7 ml. of water. A part of the sodium hydroxide goes into solution. Crude dl-2-amino-1-butanol hydrochloride 50 g. (70 percent real, 0.28 mole) is added with stirring over a period of 0.5 hr. The reaction mixture warms up to about 45°C. and crystalline sodium chloride precipitates out of the reaction mixture. The salt is removed by filtration, washed with isopropanol and the washings are combined with the main filtrate. The filtrate is distilled under reduced pressure. Isopropanol and water are removed as a fore-run and dl-2-amino-1-butanol (25 g. 88.3 percent yield) is distilled at 95°–105° at 30 mm. Gas liquid chromatographic analysis of this product showed it to contain about 10% 1-amino-2-butanol.

EXAMPLE 10 d-2-Amino-1-butanol

To a 15 g. portion of undistilled crude dl-2-amino-1-butanol (59% real, 0.1 mole) from a run similar to that of Example 2, dissolved in 48 ml. of methanol is added with stirring 17.5 g. (0.117 mole) of L(+)- tartaric acid while the temperature is maintained at 45°. The solution is seeded with a small amount of crystals of the L(+)- tartrate of d-2-amino-1-butanol and the temperature maintained at 45°C. for 0.5 hr. An additional 4.2 g. (0.028 mole) of tartaric acid is added and the mixture held at 45°–47°C. for an additional 0.5 hour. The temperature is then lowered to 16°–18° over a 4 hour period and held at this temperature for 1 hour. The crystalline L(+)- tartrate of d-2-amino-1-butanol is removed by filtration, washed with cold methanol (3 ml. × 3) and dried in an inert atmosphere. In one such run the d-2-amino-1-butanol L(+)- tartrate weighed 8.5 (0.035 mole, 71.0 percent), melted at 137°–138° and had a specific rotation $[\alpha]_D^{26} = 23.74$ (c — 5%, H$_2$O). The crude feed dl-2-amino-1-butanol contained about 8% of dl-1-amino-2-butanol as an impurity. This impurity is not carried through the resolution process. The L(+)- tartrate salt of d-2-amino-1-butanol obtained after resolution is found to contain no detectable quantities of 1-amino-2-butanol, by gas liquid chromatography, which is sensitive to about 0.01% of 1-amino-2-butanol.

EXAMPLE 11 d-2-Amino-1-butanol

To 15 g. of distilled dl-2-amino-1-butanol (88.5 percent pure by gas liquid chromatography), from a run similar to Example 2, dissolved in 48 ml. of anhydrous methanol is added with stirring 17.5 g. (0.117 mole) of L(+)- tartaric acid while maintaining the temperature below 47°C. The resulting solution is stirred at 45°–47° for 0.5 hour and an additional 4.21 g. (0.028 mole) of tartaric acid is added and the solution stirred for an additional 0.5 hour at 45–47 percent. The solution is seeded with a small amount of the L(+)- tartrate of d-2-amino-1-butanol. The mixture is slowly cooled to 16°–17°C. over a 4 hour period and the crystalline L(+)- tartrate salt of d-2-amino-1-butanol is removed by filtration, washed with cold methanol (3 ml. × 3) and dried in an inert atmosphere. The white crystalline material (14.5 g., 0.061 mole 81.9 percent yield) melts at 136°–140° and has a specific rotation of $[\alpha]_D^{25} = 23.74$ (c = 5%, H$_2$O). The feed dl-2-amino-1-butanol used for resolution contains about 8% of dl-1-amino-2-butanol as an impurity. This impurity is, however, not carried through the resolution process. The L(+)- tartrate salt of d-2-amino-1-butanol obtained after resolution is found to contain no detectable quantities of either d or l 1-amino-2-butanol by gas liquid chromatography which is sensitive to 0.01% of 1-amino-2-butanol. Apparently, all of the dl-1-amino-2-butanol remains with the mother liquor, and is rejected along with the l-2-amino-1-butanol in the methanol.

EXAMPLE 12 dl-2-Amino-1-butanol

A. A 137-g. sample of crude dl-2-amino-1-butanol hydrochloride from a run similar to Example 1 is treated with a solution of 137 g. KOH in 200 ml. of water. The mixture is extracted three times with tetrahydrofuran and the combined extracts dried (Na$_2$SO$_4$). The solvent is removed under reduced pressure to give 95 g. of a crude oil (60.6% dl-2-amino-1-butanol and 6% dl-1-amino-2-butanol).

B. In a separate experiment a 250-g. sample of similar crude dl-2-amino-1-butanol hydrochloride dissolved in 200 ml. of anhydrous methanol is treated with 3 moles of anhydrous ammonia. After a few hours stirring, the excess ammonia is allowed to evaporate. The precipitated ammonium chloride is removed by filtration and the filtrate concentrated gives 174.5 gm. of an oil which contains both dl-2-amino-1-butanol and its hydrochloride together with some quantities of dl-1-amino-2-butanol and its hydrochloride (total 58.9% dl-2-amino-1-butanol by gas liquid chromatography.

C. A 7.5-gm. sample of crude dl-2-amino-1-butanol from the first experiment (A) is mixed with a 7.5 gm. portion of the material (dl-2-amino-1-butanol and its hydrochloride) from the second experiment and the mixture is dissolved in a mixture of 80 parts of anhydrous methanol and 20 parts of isopropanol (v/v) (the solution contains 0.1 mole of real dl-2-amino-1-butanol of which 0.097 mole is present as the free base). L(+)- tartaric acid (15 g., 0.1 mole) is added slowly keeping the temperature below 45°C. until the exotherm ceases. After stirring the solution for an hour at 45°C., the temperature is lowered slowly and at 40°C. the mixture is seeded with a small amount of the L(+)- tartrate salt of d-2-amino-1-butanol and then gradually cooled to 18° over a period of 4 hours. The crystalline L(+)- tartrate salt of d-2-amino-1-butanol formed in the reaction mixture is removed by filtration, washed with cold methanol (3 ml. × 3) and pumped dry. The yield of the material is 9.0 g. (0.036 mole, 75.2 percent; m.p., 137.5°–139.5°; $[\alpha]_D^{25} = 23.84°$ (c = 5%, H$_2$O).

EXAMPLE 13

N-[1-(Chloromethyl)propyl]acetimidoyl chloride

Reagent grade acetonitrile (82 g., 2 moles) is placed in a 500 ml. three-necked flask equipped with a mechanical stirrer, a low-temperature thermometer and two fritted inlet tubes. With vigorous stirring and cooling (−20°C.), butene-1 (28 g. 0.5 mole) and chlorine (35.5 g., 0.5 mole) are added simultaneously both at a rate of about 375–400 ml./min. The addition is complete in about 37 minutes and the reaction temperature at the end of this period rises to −10°C. (bath/20°C.) The mixture is fractionated to give: Fraction I, 89 g. (mostly acetonitrile) distilling under 20 mm. pressure at a bath temperature of 50°C.; Fraction II, 12.5 g. distilling under 20 mm. pressure at a bath temperature of 65°C., 70% 1,2-dichlorobutane, 30% N-[1-chloromethyl)propyl]-acetimidoyl chloride; Fraction III, 35.9 g. distilling under 2 mm. pressure at a bath temperature of 60 °, about 90% N-[1-chloromethyl)propyl]acetimidoyl chloride residue, 6.7 g. dark brown viscous oil. Based on Fractions II and III, the yield of N-[1-(chloromethyl)propyl]acetimidoyl chloride is 39.7 g. (48%). A portion of Fraction III is redistilled to give a pale yellow oil with a characteristic odor resembling that of thionyl chloride. The product, N-[1-chloromethyl)-propyl]acetimidoyl chloride displays strong infrared bands at 3000, 1705, 1430, 1370, 1085, 960, 920, 840 and 740 cm$^{-1}$. NMR(CDCL$_3$): 0.88 ppm (t,3H), 1.4–1.8 ppm (m,2H), 245 ppm (s,3H), 3.62 ppm (m,2H,—CH$_2$Cl), and about 3.9 ppm (m,1H, CH).

Occasionally, a solid isomer of N-[1-(chloromethyl)propyl]acetimidoyl chloride (often the major product) is also obtained. The two forms seem to be interconvertible in certain solvents. On reaction with water, both hydrolyze to N-[1-chloromethyl)propyl]acetamide. The solid form has infrared bands at 3000, 1650, 1550, 1480, 1365, 1280, 1045, and 740 cm$^{-1}$.

EXAMPLE 14

N-[1-(Chloromethyl)propyl]acetamide

A sample of N-[1-chloromethyl)propyl]acetimidoyl chloride from Example 8 is treated with an excess of 10% aqueous sodium carbonate solution at room temperature. The organic material is extracted with ether and dried over $MgSO_4$. Removal of the solvent under reduced pressure leaves N-[1-(chloromethyl)propyl]acetamide as a crystalline solid in nearly quantitative yield. An infrared spectrum shows peaks at 3300(M), 3100(W), 1650(S), and 550(S) $cm^{-1}$; nuclear magnetic resonance ($CDCl_3$) shows peaks 0.95 ppm ($t$,3H), 1.4–1.8 ppm ($m$,2H), 2.03 ppm ($s$,3H), 3.67 ppm ($d$,2H,$CH_2Cl$), 3.8–4.4 ppm ($m$,1H).

The effects of conditions on yields is shown in the following examples in which the chlorination reactions were carried out at initial temperatures of $-3°$ to $+23°$ and the acetonitrile to $Cl_2$ ratio was varied from 2 to 4. Additionally, the initial concentration of butene-1 was varied by either passing butene-1 and $Cl_2$ simultaneously (low initial butene-1 concentration) into acetonitrile or by first condensing butene at $-5°C$. into acetonitrile and then passing $Cl_2$ through the mixture (high initial butene-1concentration). The results of these experiments in Table I show that the yield of N-[1-(chloromethyl)propyl]acetimidoyl chloride is dependent primarily on the mole ratio of acetonitrile to $Cl_2$ and amounts to about 50–55% when this ratio approaches 4.

nol or ethanol, it is complete within 2 hours and the acetyl component of the product can be removed as methyl or ethyl acetate by distillation. This procedure not only decreases hydrolysis time, it also avoids the accumulation of salts in the reaction mixture, gives essentially quantitative yields of dl-2-amino-1-butanol from N-[1-(chloromethyl)propyl]acetimidoyl chloride through N-[1-(chloromethyl)propyl]acetamide, and facilitates product work-up. Methyl acetate boils at 57°C., and is readily distilled off.

In order to make this process as economical as possible, excessively large volumes of aqueous methanol should be avoided. If insufficient quantities of water are used (less than N-[1-(chloromethyl)propyl]acetimidoyl chloride: $H_2O$:MeOH mole ratio 1:3:3) and especially if the hydrolysis is carried out in the presence of the 1,2-dichlorobutane by-product, a small fraction (3–15%) of N-[1-(chloromethyl)propyl]acetimidoyl chloride hydrolyzes to 2-amino-1-chlorobutane hydrochloride. The formation of 2-amino-1-chlorobutane hydrochloride can be totally suppressed if water and methanol are added sequentially, and in that order, rather than together in one step. Addition of water to N-[1-(chloromethyl)propyl]acetimidoyl chloride almost instantaneously converts it to the N-[1-(chloromethyl)propyl]acetamide which then hydrolyzes via the oxazoline intermediate.

Three series of reactions (A, B, and C) were completed using as-is acetonitrile (water conc. (Karl-Fisher) = 0.059–0.2%). In each of these series, reac-

TABLE I

PRODUCTION OF N-[1-(CHLOROMETHYL)PROPYL]ACETIMIDOYL CHLORIDE (I)
Reaction of Butene-1 (0.5 mole) with $Cl_2$ (0.5 mole) in Acetonitrile[a] (AN)

| Example | T°C Init. | T°C Peak | AN/Cl (mole ratio) | $Cl_2$ Rate (ml/min) | Reaction Time (hrs.) | Initial Butene conc. | I (% yield)[d] |
|---|---|---|---|---|---|---|---|
| 15 | 0 | 3 | 2 | 100 | 2 | high[b] | 36 |
| 16 | 0 | 17 | 2 | 100 | 2 | low[c] | 37.8 |
| 17 | 23 | 27 | 4 | 400 | 0.5 | low[c] | 57.0 |
| 18 | −2 | 20 | 4 | 400 | 0.5 | high[b] | 43.8 |
| 19 | −3 | 32 | 4 | 400 | 0.5 | high[b] | 48.0 |
| 20 | 0 | 5 | 4 | 400 | 0.5 | high[b] | 54.0 |
| 21 | 0 | 5 | 4 | 100 | 2.0 | low[c] | 55.0 |

[a]All reactions were carried out in a Morton flask under vigorous stirring and at atmospheric pressures.
[b]Butene-1 was charged to reaction flask by pouring a weighed sample into acetonitrile cooled to −5°C.
[c]Butene-1 and $Cl_2$ were simultaneously passed via calibrated flowmeters.
[d]Yields were based on actual weights of the residues left after distilling off the volatiles. Product purity was checked by gas liquid chromatography, infrared, and nuclear magnetic resonance.
(I)I = N-[1-(chloromethyl)propyl]acetimidoyl chloride.

Hydrolysis of N-[1-(chloromethyl)propyl]acetimidoyl chloride is highly pH dependent. It has now been found that a simple hydrolysis procedure is effective. On refluxing with water N-[1-(chloromethyl)propyl]acetimidoyl chloride is transformed into a mixture of dl-2-amino-1-butanol (77%), dl-2-amino-1-butanol acetate hydrochloride (17%), the N-[1-(hydroxymethyl)propyl]acetamide (7%) and acetic acid within one hour. The product ratios appear to represent equilibrium compositions because additional heating (14 hrs.) does not materially change their distribution. If, however, the hydrolysis is carried out with aqueous methations were carried out using 0.5 mole of butene, 0.5 mole of chlorine, and the acetonitrile:$Cl_2$ mole ratio (identical to the acetonitrile: butene) was varied from 1 to 8.

In series A (reaction time = 1 hr.) the reaction temperature was maintained at 0°C. while chlorine and butene were passed simultaneously into acetonitrile in one hour. After removal of acetonitrile (40°–50°, 50 mm), the crude reaction mixture containing N-[1-(chloromethyl)propyl]acetimidoyl chloride and 1,2-dichlorobutane was hydrolyzed by refluxing with aqueous methanol.

TABLE II

| Example | T°C. | Moles Butene | AN[a]/Butene/$Cl_2$ Mole Ratio | $Cl_2$ Rate (ml/min) | Reaction Time (hrs.) | % yield of crude 2-amino-1-butanol hydrochloride |
|---|---|---|---|---|---|---|
| 22 | 0° | 1.0 | 1:1:1 | 400 | 1.0 | 31.6 |

TABLE II-continued

| Example | T°C. | Moles Butene | AN[a]/Butene/Cl$_2$ Mole Ratio | Cl$_2$ Rate (ml/min) | Reaction Time (hrs.) | % yield of crude 2-amino-1-butanol hydrochloride |
|---------|------|--------------|-------------------------------|----------------------|----------------------|--------------------------------------------------|
| 23 | 0° | 0.5 | 2:1:1 | 200 | 1.0 | 43.6 |
| 24 | 0° | 0.5 | 4:1:1 | 200 | 1.0 | 52.5 |
| 25 | 0° | 0.5 | 6:1:1 | 200 | 1.0 | 61.0 |
| 26 | 0° | 0.5 | 8:1:1 | 200 | 1.0 | 67.0 |

[a]AN = Acetonitrile

It is significant to note that N-[1-(chloromethyl)-propyl]acetimidoyl chloride can be hydrolyzed substantially quantitatively to N-[1-(chloromethyl)propyl]acetamide, and then to dl-2-amino-1-butanol. Reporting as dl-2-amino-1-butanol hydrochloride is a very convenient method of showing yields. Errors due to volatile components are avoided. Small quantities of dl-1-amino-2-butanol report with the dl-2-amino-1-butanol. Even at a low acetonitrile:Cl$_2$ ratio of one, the yield of dl-2-amino-1-butanol.HCl is as high as 31%. Increasing the acetonitrile:Cl$_2$ mole ratio from 1 to 2 improves the yield to 43 percent, an increase of 12 percent. Further increases in the acetonitrile:Cl$_2$ ratios also improve the yields. For each additional mole of acetonitrile (up to a total of 5 moles (AN:Cl$_2$ ratios 3 to 5) the yield of dl-2-amino-1-butanol.HCl increases on average about 6 percent. Still further addition of acetonitrile (AN:Cl$_2$ mole ratios 6 to 8) is considerably less effective; the average incremental yield of dl-2-amino-1-butanol.HCl being of the order of about 3% per mole of acetonitrile. A ratio of about 4:1 is a good compromise between yield and a reasonable size reaction vessel and recycle ratio of acetonitrile.

In both series B and C, the gaseous reactants were run into acetonitrile over a period of 0.5 hr. The initial reaction temperature was 0°. This was allowed to rise to a maximum of 35° during the course of the reaction. Additionally, in series B, chlorine was passed through a solution of butene in acetonitrile to maintain a high initial concentration of butene. In series C both chlorine and butene were passed simultaneously through acetonitrile allowing attainment of a low initial concentration of butene. The results of simultaneous and sequential additions of butene and chlorine on the yield of N-[1-chloromethyl)propyl]acetimidoyl chloride at different acetonitrile/Cl$_2$ mole ratios are summarized in Table III.

TABLE III

Reaction of Butene-1 (0.5 mole)[a] with Cl$_2$ (0.5 mole)[a] in Acetonitrile (AN)
Series B[b]: Addition of Cl$_2$ to Butene + Acetonitrile (AN)

| Example | T°C. | AN:Cl$_2$ (mole ratio) | N-[1-(chloromethyl)-propyl]acetimidoyl chloride Moles | N-[1-(chloromethyl)-propyl]acetimidoyl chloride %[c] | 1,2-dichlorobutane (moles) | N-1-(chloromethyl-propyl]acetimidoyl chloride + 1,2-dichlorobutane (moles) Exp. | N-1-(chloromethyl-propyl]acetimidoyl chloride + 1,2-dichlorobutane (moles) Theor. | % acetonitrile recovery |
|---------|------|------------------------|--------------------------------------------------------|-------------------------------------------------------|----------------------------|--------------------------------------------------------------------------------|----------------------------------------------------------------------------------|-------------------------|
| 27 | 0–35 | 1.1 | 0.164 | 32.3 | 0.350 | 0.514 | 0.5 | 90 |
| 28 | 0–30 | 1.5 | 0.162 | 32.6 | 0.340 | 0.502 | 0.5 | 92 |
| 29 | 0–25 | 2 | 0.192 | 38.0 | 0.310 | 0.502 | 0.5 | 97 |
| 30 | 0–23 | 4 | 0.223 | 45.3 | 0.250 | 0.473 | 0.5 | 95 |
| 31 | 0–25 | 4 | 0.241 | 47.8 | — | — | — | — |
| 32 | 0–23 | 6 | 0.291 | 57.6 | 0.270 | 0.561 | 0.5 | 94 |
| 33 | 0–15 | 8 | 0.269 | 54.3 | 0.180 | 0.459 | 0.5 | 99 |
| Series C[b]: Simultaneous Addition of Cl$_2$ and Butene to Acetonitrile | | | | | | | | |
| 34 | 0–25 | 1 | 0.74 | 35.6 | 1.26 | 2.00 | 2.0 | 102 |
| 35 | 0–24 | 2 | 0.222 | 43.9 | 0.270 | 0.492 | 0.5 | 99 |
| 36 | 0–27 | 4 | 0.246 | 47.1 | 0.270 | 0.516 | 0.5 | 99 |
| 37 | 0–22 | 6 | 0.281 | 54.0 | 0.240 | 0.521 | 0.5 | 97 |
| 38 | 0–21 | 8 | 0.337 | 66.0 | 0.130 | 0.467 | 0.5 | 99 |

[a]Except in Example 34 where 2 mole of Cl$_2$ and 2 mole of butene were passed through 2 moles of acetonitrile over a two-hour period.
[b]Reaction time: 0.5 hr; Cl$_2$ rate: 400 ml/min
[c]Yields based on butene. These percentages do not include losses of N-[1-(chloromethyl)propyl]-acetimidoyl chloride during removal of 1,2-dichlorobutane by distillation which may amount to 3–5%.

In series B and C material balances show conversion and recovery data on acetonitrile. In each case the distillate 1,2-dichlorobutane + acetonitrile was analyzed for 1,2-dichlorobutane and acetonitrile by gas liquid chromatography.

A less pure product is obtained if the N-[1-(chloromethyl)propyl] acetimidoyl chloride is allowed to stand for 40–50 hours prior to work-up.

The data in the table shows that:

1. The yield of crude dl-2-amino-1-butanol.HCl (or N-[1-(chloromethyl)propyl]acetimidoyl chloride) is primarily dependent on the mole ratio of acetonitrile:Cl$_2$ and varies between 31 and 66% as the acetonitrile:Cl$_2$:butene mole ratio changes from 1:1:1 to 8:1:1.
2. Simultaneous addition of chlorine and butene to acetonitrile rather than the alternate procedure of adding chlorine to a mixture of butene and acetonitrile is advantageous. The reaction is less exothermic, consequently easier to control, and the yields of dl-2-amino-1-butanol.HCl are somewhat better. A reaction time of one hour generally appears to permit more control over the reaction exothermicity.
3. The reaction temperature does not appear to be a controlling factor in determining the overall yield. However, in view of the thermal instability of N-[1-(chloromethyl)propyl]acetimidoyl chloride) above 50°, reaction temperatures between 0°–25° are more desirable.

The process can vary depending on the size of batches. Whereas the Examples are exemplary, for large scale production, the process may be run continuously with the butene-1 and chlorine being fed continuously to a stirred continuous reactor. The recycle acetonitrile is distilled off and recycled continuously. Such a continuous system permits a higher ratio of acetonitrile to the butene-1 and chlorine. Whereas, for a batch process, a molar ratio of at least 2 of acetonitrile to butene-1 and chlorine is preferred, more than a ratio of 16 can require an uneconomically large reactor. With a continuous process even higher ratios are convenient.

Whereas both butene-1 and chlorine are gaseous at room temperature of about 20°C., so that low temperatures, around 0°C. and lower are convenient, a higher temperature to reduce the need for cooling may be used if a pressurized reactor is available.

The trade-off of the cost of a pressure reactor against additional refrigeration can vary with equipment available.

Other modifications within the scope of this invention as defined by the appended claims are, of course, obvious to those skilled in the arts.

I claim:

1. A process for the synthesis of N-[1-(chloromethyl)propyl]acetamide which comprises reacting N-[1-(chloromethyl)propyl]acetimidoyl chloride with water, in the presence of at least about a molar equivalent of a weak base selected from the group consisting of calcium carbonate, calcium oxide, calcium hydroxide, sodium carbonate, sodium bicarbonate, potassium carbonate, potassium bicarbonate, barium carbonate, and strontium carbonate, thereby hydrolyzing N-[1-(chloromethyl)propyl]acetimidoyl chloride to N-[1-(chloromethyl)propyl]acetamide.

2. In the synthesis of N-[1-(chloromethyl)propyl]acetamide by the reaction of butene-1, chlorine and acetonitrile to form N-[1-(chloromethyl)propyl]acetimidoyl chloride, with the concurrent by-product production of 1,2-dichlorobutane, and the hydrolysis of said N-[1-(chloromethyl)propyl]acetimidoyl chloride to N-[1-(chloromethyl)propyl]acetamide, the improvement comprising:

adding sufficient water in the presence of at least about a molar equivalent of a weak base selected from the group consisting of calcium carbonate, calcium oxide, calcium hydroxide, sodium carbonate, sodium bicarbonate, potassium carbonate, potassium bicarbonate, barium carbonate, and strontium carbonate to hydrolyze N-[1-(chloromethyl)propyl]acetimidoyl chloride to N-[1-(chloromethyl)propyl]acetamide, and distilling off under reduced pressure acetonitrile and 1,2-dichlorobutane.

3. A process for the synthesis of N-[1-(chloromethyl)propyl]acetamide which comprises reacting at least about 2 moles of acetonitrile with about 1 mole of chlorine and about 1 mole of butene-1, to produce N-[1-(chloromethyl)propyl]acetimidoyl chloride with the concurrent production of 1,2-dichlorobutane, adding water in the presence of at least about a molar equivalent of a weak base selected from the group consisting of calcium carbonate, calcium oxide, calcium hydroxide, sodium carbonate, sodium bicarbonate, potassium carbonate, potassium bicarbonate, barium carbonate, and strontium carbonate, thereby hydrolyzing said N-[1-(chloromethyl)propyl]acetimidoyl chloride to N-[1-(chloromethyl)propyl]acetamide, and after the synthesis of said N-[1-(chloromethyl)propyl]acetamide, distilling off under reduced pressure and recovering the excess acetonitrile.

4. The process of claim 3 in which water is added at about the same rate as N-[1-(chloromethyl)propyl]acetimidoyl chloride is produced, thereby hydrolyzing to N-[1-(chloromethyl)propyl]acetamide before said N-[1-(chloromethyl)propyl]acetimidoyl chloride can be additionally chlorinated, and also releasing the heat of hydrolysis over the course of the reaction, thus controlling isothermal temperature rise.

5. The process of claim 4 in which the separated acetonitrile is recycled without additional purification.

6. The process of claim 5 in which the addition of butene-1, chlorine and water to acetonitrile is a continuous process, and the recycling of acetonitrile is continuous.

* * * * *